United States Patent [19]
Jarverud et al.

[11] Patent Number: 5,556,419
[45] Date of Patent: Sep. 17, 1996

[54] IMPLANTABLE CARDIAC STIMULATOR WITH ANALYZER THAT CONTINOUSLY COMPARES RADIUS OF DERIVED HEART SIGNAL

[75] Inventors: Karin Jarverud, Stockholm; Kjell Noren, Solna, both of Sweden

[73] Assignee: Pacesetter AB, Solna, Sweden

[21] Appl. No.: 342,051

[22] Filed: Nov. 17, 1994

[30] Foreign Application Priority Data

Dec. 3, 1993 [SE] Sweden ................................. 9304029

[51] Int. Cl.$^6$ .......................... A61B 5/04; A61N 1/36; A61N 1/362
[52] U.S. Cl. .................................. 607/9; 128/699
[58] Field of Search ................... 607/9; 128/699

[56] References Cited

U.S. PATENT DOCUMENTS

| | | | |
|---|---|---|---|
| 4,457,315 | 7/1984 | Bennish | 128/704 |
| 4,700,712 | 10/1987 | Schmid | 128/699 |
| 4,754,753 | 7/1988 | King | 128/699 |
| 4,905,705 | 3/1990 | Kizakevich et al. | 128/696 |
| 5,101,833 | 4/1992 | Schmid | 128/699 |
| 5,306,293 | 4/1994 | Zacouto | 607/17 |
| 5,413,109 | 5/1995 | Ekwall | 128/696 |
| 5,427,112 | 6/1995 | Noren et al. | 128/699 |

FOREIGN PATENT DOCUMENTS

| | | | |
|---|---|---|---|
| 2213729 | 8/1989 | United Kingdom | A61N 1/365 |
| 2219508 | 12/1989 | United Kingdom | A61N 1/365 |

OTHER PUBLICATIONS

"Phase Plane Plot of Electrograms as a Marker of Ventricular Electrical Instability During Acute Ischemia: Initial Experimental Results and Potential Clinical Applications," Karagueuzian et al., PACE, vol. 15, Nov. 1992, pp. 2188–2193.

*Primary Examiner*—William E. Kamm
*Assistant Examiner*—Carl H. Layno
*Attorney, Agent, or Firm*—Hill, Steadman & Simpson

[57] ABSTRACT

A device for identifying abnormal conditions in a heart retrograde conduction and tachyarrhythmias in particular, includes a differentiating circuit electrically connected to a heart to be monitored in order to differentiate ECG signals from the heart. The differentiated signal is plotted against the ECG signal. The radius (distance from a point on the resulting curve from the origin of the plot axes) in the resulting curve is calculated in a calculator unit. The radius obtained is then compared with a threshold value in a comparator and a sequence for the progression of the radius in relation to the threshold value is obtained and compared with previously obtained sequences stored in a sequence analyzer.

22 Claims, 4 Drawing Sheets

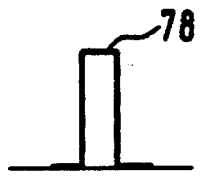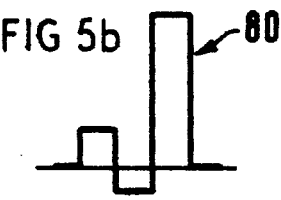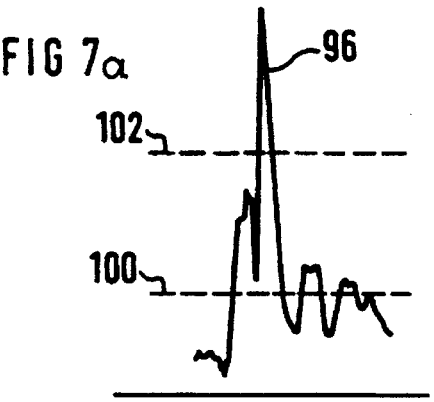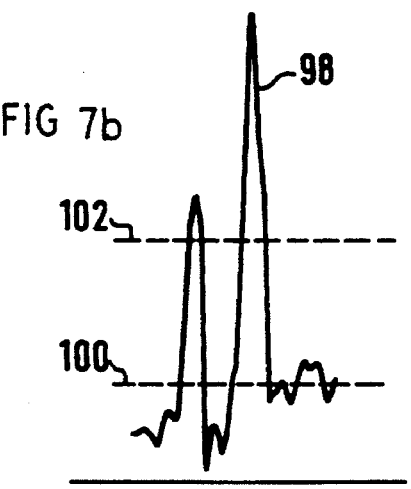

5,556,419

IMPLANTABLE CARDIAC STIMULATOR WITH ANALYZER THAT CONTINOUSLY COMPARES RADIUS OF DERIVED HEART SIGNAL

BACKGROUND OF THE INVENTION

1. Field of the Invention

The present invention relates to a device for analyzing electrical signals from a heart of the type having a measurement unit for generating a measurement signal related to the electrical activity of the heart and an evaluation unit for identifying abnormal conditions in the heart on the basis of the measurement signal.

The present invention also relates to a heart stimulator, embodying such an analysis device, for detecting and treating tachyarrhythmias in a heart.

2. Description of the Prior Art

In the diagnosis and treatment of patients with various abnormalities in cardiac function, the ability to make reliable distinctions between normal and abnormal events in the heart is important. The heart's intrinsic signals, i.e. the ECG signals, have long been used for distinguishing between normal and various abnormal conditions.

The ability to distinguish normal heart conditions from abnormal conditions is especially important in the case of tachyarrhythmias. Examination of the heart rate alone is not enough for a reliable determination of whether a tachyarrhythmia is present. Some hearts manage to operate normally at rates up to about 200 beats a minute, whereas other hearts develop unstable tachyarrhythmias at rates of only 100–120 a minute. Thus the use of parameters other than the heart rate is necessary for establishing whether a heart is afflicted by unstable tachyarrhythmia.

Retrograde conduction from a ventricle to an atrium is another cardiac defect for which identification is important. Retrograde conduction impairs the heart's pumping capacity and can trigger PMT's (pacemaker mediated tachycardia), i.e. a tachycardia evoked and sustained by a heart stimulator.

SUMMARY OF THE INVENTION

An object of the present invention is to achieve an analysis device for reliable identification of abnormal conditions in a heart.

Another object of the present invention is to achieve a heart stimulator which can be used for diagnosing and treating tachyarrhythmias.

One such analysis device is achieved in accordance with the invention wherein a measurement signal from a heart, obtained by a measurement unit, is supplied to a differentiating circuit connected to the measurement unit, in which the (first) derivative of the measurement signal is formed. An evaluation unit is connected to the measurement unit and to the differentiating circuit in order to obtain both the measurement signal and the derivative of the measurement signal as input signals. The evaluation continuously determines the radius from an origin to the curve which ensues by means of the measurement signal and the derivative of the measurement signal being used as coordinates for points in a coordinate system. The evaluation unit identifies abnormal conditions on the basis of changes in the radius for each heart cycle.

The ECG signal, used as the measurement signal in the present invention, does not always display a difference between normal heart conditions and a tachyarrhythmia or some other abnormal cardiac condition which is large enough to permit reliable discrimination of the different conditions. Utilizing the derivative of the ECG signal and plotting the ECG signal against its derivative yields a closed curve for each heart cycle. The radius of the curve at any given time and as a progression during a cardiac cycle, designates the differences between different heart conditions far more distinctly than the ECG signal, or its derivative, taken alone. Normal heart function, retrograde conduction and various tachyarrhythmias in particular then display a clear, distinct difference in the curves obtained from the ECG signal and its derivative. This is mainly because the normal state is inherently stable and supplies a curve which is virtually identical for each heart cycle, which is also the case for retrograde conditions and various tachyarrhythmias, i.e. they produce, in principle, the same sequence of changes in the radius of the said curves in each heart cycle. These different conditions can therefore be easily identified and distinguished from each other.

Preferably the evaluation unit identifies abnormal conditions on the basis of the changes in radius as a function of the time for each heart cycle. This will increase the system's ability to analyze different courses in which the radius changes for various abnormal conditions.

A refinement of the analysis device is achieved in accordance with the invention wherein the evaluation unit includes a comparator which compares the radius with a threshold value. Since the change in radius during a heart cycle will vary widely in different conditions, introduction of a threshold value with which the radius is compared is advantageous.

This comparison becomes especially advantageous in an embodiment wherein the evaluation unit further includes means for determining a sequence of time intervals during which the radius is respectively above or below the threshold value, and a RAM in which the sequence is stored, and wherein the evaluation unit identifies abnormal conditions by comparing the most recently identified sequence with previously stored sequences.

The identified sequence designates how the radius changes in relation to the threshold value, i.e. how long the radius was above the threshold value and whether it passed the threshold value a plurality of times during one heart cycle. This supplies a "fingerprint" for normal and abnormal conditions in every individual heart.

It is advantageous if the threshold value is set at a value related to the maximum radius during the current cardiac cycle, preferably 50% of the maximum radius.

In another embodiment of the analysis device in accordance with the invention, the evaluation unit has at least one additional comparator which compares the radius with at least one additional threshold value. Even in this instance it is especially advantageous if the evaluation unit also determines a sequence for the period of time during which the radius is above, below and between the threshold values, stores this information in the RAM, and the evaluation unit identifies abnormal conditions by comparing the latest identified sequence with previously stored sequences.

This results in accurate identification of even more conditions in the heart.

A heart stimulator for detecting and treating tachyarrhythmias is achieved in accordance with the invention having a pulse generator for generating and emitting stimulation pulses, an electrode system for delivering the stimulation pulses to heart tissue, a detector for detecting tachyarrhythmias and a control device for controlling the pulse generator's generation and emission of stimulation pulses when tachyarrhythmia is detected, with the detector being an analysis device as described in any of the above embodiments.

The heart stimulator can naturally also be devised to identify retrograde condition and prevent the development of PMT with an analysis device according to any of the above embodiments.

DESCRIPTION OF THE DRAWINGS

FIGS. 5a and 5b are is a bar charts showing the relation of the radii to the threshold values in accordance with the invention.

FIG. 6 shows a second embodiment of the analysis device of the invention.

FIGS. 7a and 7b illustrate detection of retrograde conduction from an atrium in accordance with the invention.

DESCRIPTION OF THE PREFERRED EMBODIMENTS

Figure 1:
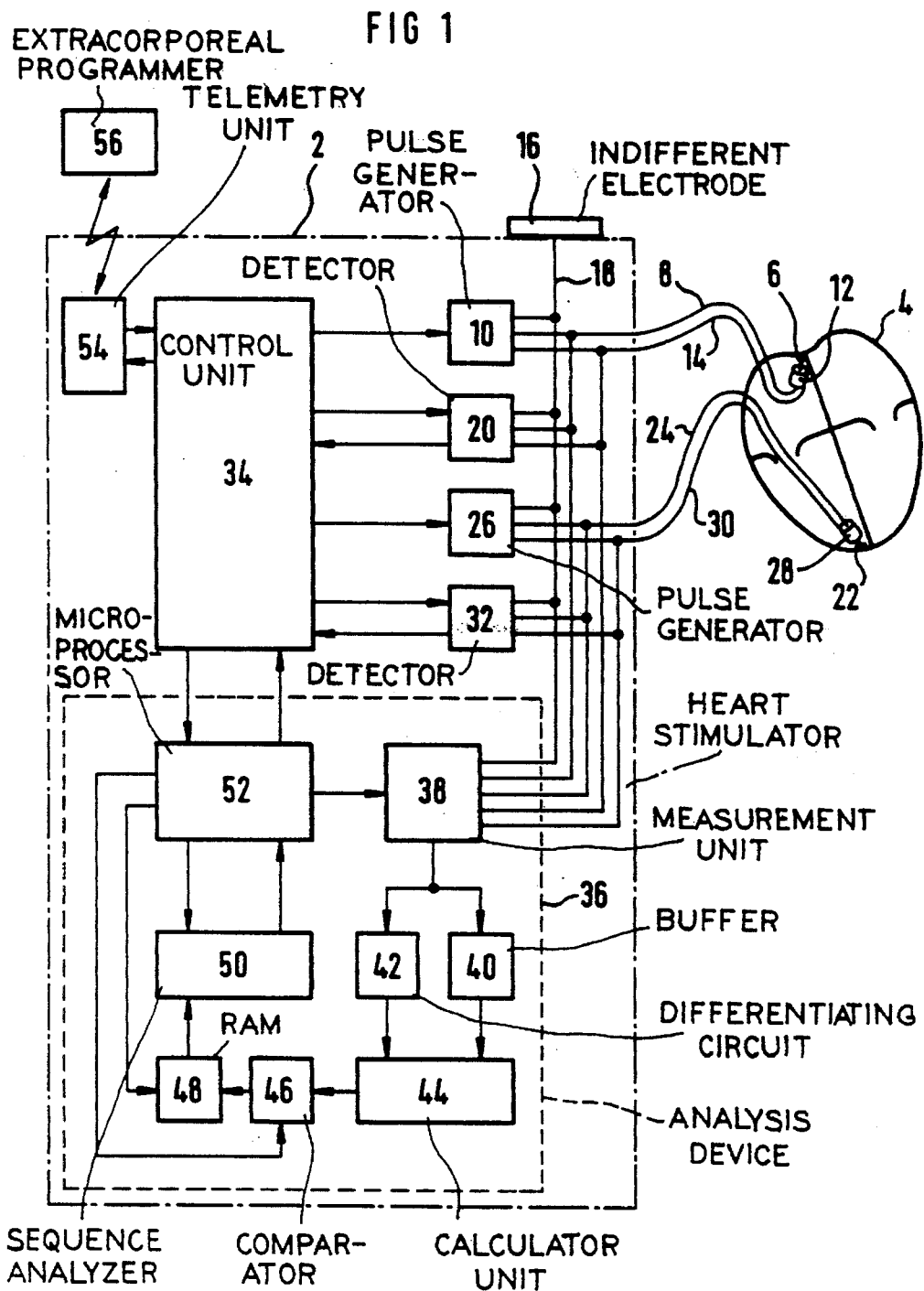
FIG. 1 shows one embodiment of a heart stimulator with an analysis device according to the invention.

A heart stimulator 2 is shown in a block diagram in FIG. 1. The heart stimulator 2 is connected to a heart 4 in order to sense heart signals and emit stimulation pulses to the heart 4. A first tip electrode 6 is anchored in an atrium of the heart 4 and connected, via a first electrode conductor 8, to a first pulse generator 10 in the heart stimulator 2. A first ring electrode 12 is connected near the first tip electrode 6 and, via a second electrode conductor 14, to the first pulse generator 10. A stimulation pulse to the atrium can be delivered to heart tissue by the first pulse generator via the first electrode conductor 8 and the first tip electrode 6. The stimulation pulse is then returned, via the first ring electrode 12 and the second electrode conductor 14, to the first pulse generator 10. Alternately, the stimulation pulse can be delivered via the first tip electrode 6 and an indifferent electrode 16 which, in this instance, consists of the enclosure of the heart stimulator 2 but can also consist of a separate electrode located somewhere in the body. The indifferent electrode 16 is connected to the first pulse generator 10 via a third electrode conductor 18 in order to return stimulation pulses from the atrium. A first detector 20 is connected in parallel across the output terminal of the first pulse generator 10 in order to sense atrial activity in the heart.

In the corresponding manner, a second tip electrode 22 is connected to a ventricle in the heart 4 and, via a fourth electrode conductor 24, to a second pulse generator 26. A second ring electrode 28 is located near the second tip electrode 22 and connected, via a fifth electrode conductor 30, to the second pulse generator 26. Delivery of a stimulation pulse to the ventricle can be bipolar via the second tip electrode 22 and the second ring electrode 28, or unipolar via the second tip electrode 22 and the indifferent electrode 16. A second detector 32 is connected in parallel across the output terminal of the second pulse generator 26 in order to sense ventricular activity in the heart.

The pulse generators 10 and 26 and the detectors 20 and 32 are controlled by a control unit 34 which regulates the stimulation pulses with respect to amplitude, duration and stimulation interval, the sensitivity of the detectors 20 and 32 etc.

In order to sense and identify abnormal conditions in the heart 4, retrograde conduction and tachyarrhythmias in particular, the heart stimulator 2 is equipped with an analysis device in accordance with the invention.

FIG. 1 shows a first embodiment of the analysis device. The analysis device 36 is connected to the first tip electrode 6 via the first electrode conductor 8, the first ring electrode 12 via the second electrode conductor 14, the second tip electrode 22 via the fourth electrode conductor 24, the second ring electrode 28 via the fifth electrode conductor 30 and the indifferent electrode 16 via the third electrode conductor 18. The electrical signals of the heart 4, i.e. the ECG signals, can be detected in unipolar fashion across the first tip electrode 6 and the indifferent electrode 16, across the first ring electrode 12 and the indifferent electrode 16, across the second tip electrode 22 and the indifferent electrode 16 or across the second ring electrode 28 and the indifferent electrode 16. Bipolar detection of the ECG signal is also possible across the first tip electrode 6 and the first ring electrode 12 or across the second tip electrode 22 and the second ring electrode 28. In addition, the electrical signals of the heart 4 can be sensed across either of the electrodes 6 and 12 in the atrium and either of the electrodes 22 and 28 in the ventricle. The analysis device 36 includes a measurement unit 38 which is capable of selectively receiving signals with any of these combinations of electrodes and which filters and amplifies the incoming signals in an appropriate manner.

The output signal from the measurement unit 38, which is proportional to the measurement signal, is then sent to a buffer 40 and to a differentiating circuit 42. Buffering is performed so the differentiated signal is in phase with the proportional signal when they are sent to a calculator unit 44. The calculator unit 44 calculates a normalized radius for the curve obtained from the two signals used as coordinates in a coordinate system. Calculated radii are sent to a comparator 46 for comparison with a threshold value. When the radius passes the threshold value the first time in each heart cycle, a process starts for determining the time during which the radius is above or below the threshold value during the part of the heart cycle in which an ECG signal is present. The sequence of time intervals obtained thereby is transferred to a RAM 48. The sequence is then compared in a sequence analyzer 50 with previously stored sequences for normal and abnormal conditions in the heart. When the sequence has been identified, the information is sent to a microprocessor 52 which communicates with the control unit 34. If, e.g., a tachyarrhythmia is identified, the control device 34 can institute therapeutic treatment with stimulation pulses to terminate the tachyarrhaythmia.

The microprocessor 52 controls the measurement unit 38 with respect to the measurement signal to be sent to the analysis device 36 and can also control both the comparator 46 for varying the threshold value and the 48 in order to store sequences not previously found in the heart, etc.

A physician using an extracorporeal programmer 56 can, via a telemetry unit 54, communicate with the heart stimulator 2 and thereby obtain information on identified conditions and also reprogram the different functions of the heart stimulator 2.

Figure 2A:
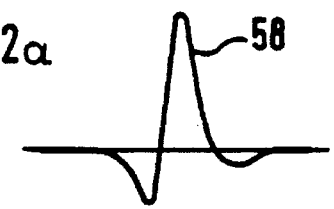
FIGS. 2a through 2d illustrate a normal ECG signal and its derivative plus an ECG signal for a tachyrhythmia and its derivative.
Figure 2C:
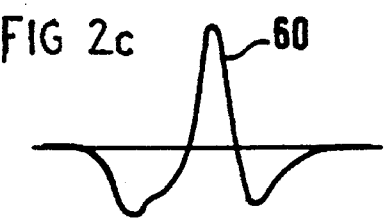
Figure 2B:
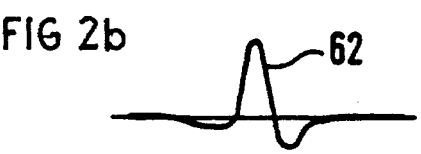
Figure 2D:
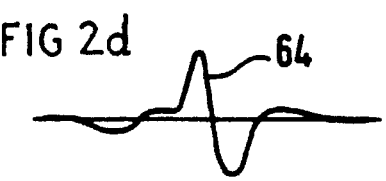
Figure 3:
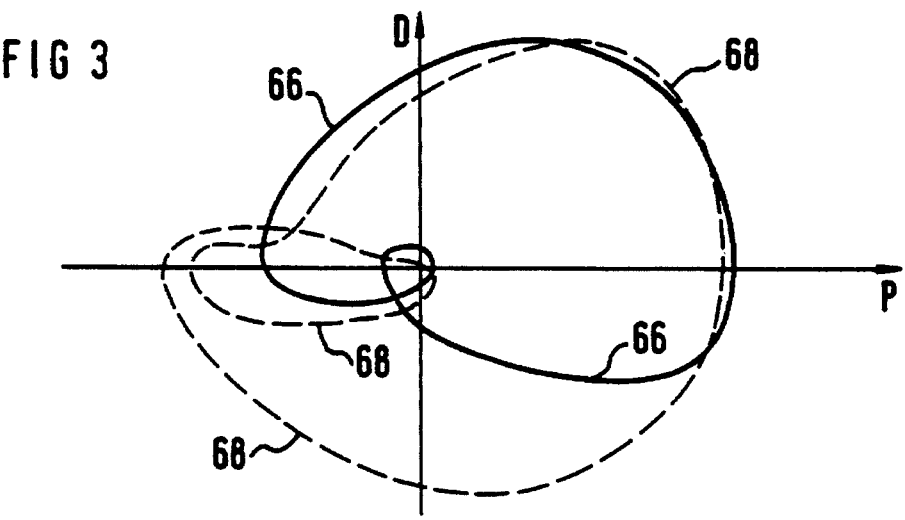
FIG. 3 is a diagram showing the curves for a normal heart sequence and for a tachyarrhythmia.

FIG. 2a shows a normal ECG signal 58 and FIG. 2c shows an abnormal ECG signal 60, in this instance a tachyarrhythmia. As FIGS. 2a and 2c show, determining whether a beat was normal or abnormal on the basis of the ECG signal is not easy. A study of the respective signal's derivative, i.e. the normal ECG signal's derivative 62 (FIG. 2b) and the abnormal ECG signal's derivative 64 (FIG. 2d), is similarly unable to reliably determine whether a heart beat was normal. Differences between the signals become apparent, however, when the signals are instead normalized and plotted against each other in a diagram with the proportional signal P on one axis and the differentiated signal D on the other axis. This is illustrated in FIG. 3 in which the normal ECG signal 58 has been plotted against its derivative 62, resulting in the curve 66. The abnormal ECG signal 60 has been plotted against its derivative 64 and results in the dashed curve 68. The clearest differences are in the lower part of the P-D diagram in which the abnormal signal curve 68 dips much lower and also has displays a much larger loop around the origin than the normal signal curve 66.

Figure 4A:
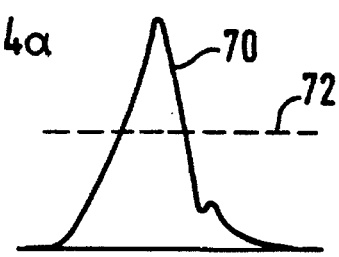
FIGS. 4a and 4b show the variation in radius of the respective curves in FIG. 3 taken over one heart cycle in accordance with the invention.
Figure 4B:
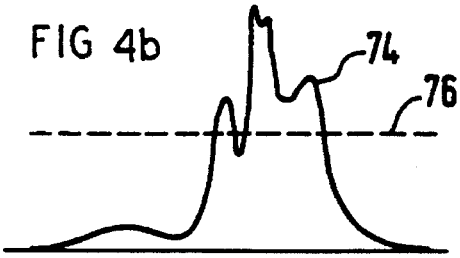

When the radius from the origin out to a location on the plotted curve is determined during a heart cycle, a simple measure is obtained of the basic, characteristic features of the respective signal. This has been performed in FIGS. 4a and 4b, which illustrates the change in the radius for the normal heart signal 70 (FIG. 4a) and the abnormal heart signal 74 (FIG. 4b) during a heart cycle. In FIGS. 4a and 4b, a first threshold value 72 has also been entered for the normal heart signal 70, this first threshold value 72 corresponding to 50% of the maximum radius during the heart cycle. In the corresponding manner, a second threshold value 76 has been entered for the abnormal heart signal 74, said second threshold values constituting 50% of the maximum radius during the abnormal heart cycle.

One simple way of identifying and discriminating the different heart conditions is to measure how long the respective radius distribution is above the threshold value during a heart cycle and whether the threshold value is crossed a plurality of times during a heart cycle. In the latter instance, the time in which the radius was on either side of the threshold value is also determined.

FIG. 5a shows a bar 78 for the normal heart signal 70 from FIG. 4a and FIG. 5b shows bars 80 for the abnormal heart signal 74 from FIG. 4b. The height of the bar 78 corresponds to the time in which the radius was above the first threshold value 72 and corresponds to a normal sequence. The bars 80 for the abnormal heart signal 74 clearly show that the sequence is completely different. When these sequences are stored in the memory of the sequence analyzer 50, each heart cycle can readily be checked as to whether it represents a normal heart cycle or tachyarrhythmia.

A second embodiment of the analysis device is shown in FIG. 6. The analysis device 82 can be incorporated into a heart stimulator in the same way as the analysis device 36 in FIG. 1 and can, in particular, be incorporated into the heart stimulator 2 in FIG. 1. The same reference designations are therefore used for the connections with other components in the heart stimulator. A measurement unit 84 can selectively receive electrical signals via any combination of the first electrode conductor 8, the second electrode conductor 14, the third electrode conductor 18, the fourth electrode conductor 24 and the fifth electrode conductor 30. The measurement signal is sent to a buffer 86 and a differentiating circuit 88. The proportional signal and the differentiated signal are then synchronously sent to a calculator unit 90 for calculation of the radius of the curve derived from the respective signal. The calculated radii are sent to a comparator unit 92 in which the radii are compared to two threshold values. The comparator unit 92 generates different output signals, depending on whether the calculated radius is under both threshold values, above one threshold value, or above both threshold values. The output signal from the comparator unit 92 is sent to an evaluation unit 94 which analyzes the output signal sequence from the comparator unit 92 for each heart cycle and compares it with previously stored sequences. The evaluation unit 94 communicates with the control device 34.

FIG. 7a shows a comparison between a radius course for a normal heart cycle 96 and FIG. 7b shows a radius course for retrograde conduction 98. The radius courses are based on signals detected in the atrium of a heart. For both courses, a first threshold value 100 and a second threshold value 102 have been marked. The differences can be clearly seen in FIGS. 7a and 7b. Retrograde conduction 98 produces a more pronounced double peak for the radius course during the heart cycle. The threshold values 100 and 102 can be selected so the output signal from the comparator unit 92 accentuates this double peak, as FIG. 7b shows.

Figure 8A:
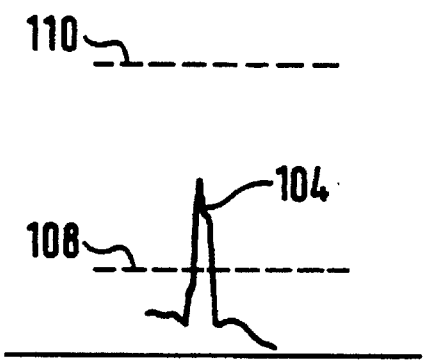
FIGS. 8a and 8b illustrates detection of retrograde conduction from a ventricle in accordance with the invention.
Figure 8B:
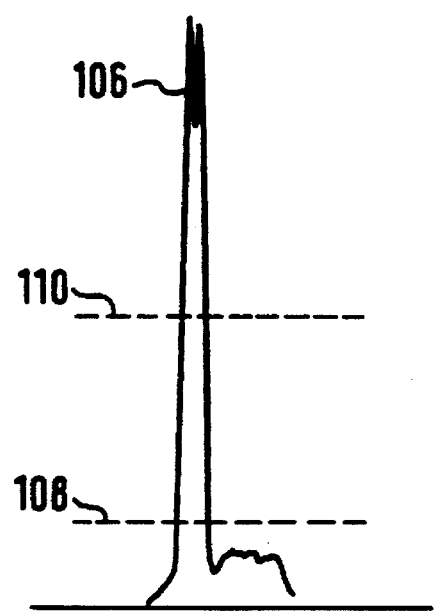

Retrograde conduction can also be identified on the basis of signals detected in a ventricle of the heart. This is illustrated in FIGS. 8a and 8b. A normal radius course 104 (FIG. 8a) and a radius course for retrograde conduction 106 are shown. Both signals are normalized. Retrograde conduction 106 clearly displays a much larger maximum radius. Reliable identification of retrograde conduction 106 is achieved if a first threshold value 108 and a second threshold value 110 are included in a suitable manner.

The analysis devices 36 and 82 can be combined into a single analysis device which performs all the functions described in the aforesaid embodiments. It can then be devised so it compares the radius to a plurality of threshold values, the time a radius is above, below or between the respective threshold values thereby being established.

The analysis devices 36 and 82 can be implemented in all forms of heart stimulators and defibrillators.

Although modifications and changes may be suggested by those skilled in the art, it is the intention of the inventors to embody within the patent warranted hereon all changes and modifications as reasonably and properly come within the scope of their contribution to the art.

We claim as our invention:

1. A device for analyzing electrical signals from a heart comprising:

measuring means for generating a measurement signal related to electrical activity of a heart;

differentiating means, connected to said measurement means and receiving said measurement signal therefrom, for forming a first derivative of said measurement signal; and evaluation means, connected to said measurement means and to said differentiating means and receiving said measurement signal and said first derivative of said measurement signal respectively therefrom, for plotting said measurement signal relative to said first derivative as coordinates in a coordinate system to obtain a resulting curve having a radius from said curve to an origin of said coordinate system, said radius exhibiting fluctuating values during each heart cycle of said heart, and for continuously monitoring said fluctuating values of said radius for identifying abnormal conditions of said heart dependent on said fluctuating values of said radius during each heart cycle.

2. An analysis device as claimed in claim 1 wherein said evaluation means comprises means for identifying abnormal conditions of said heart dependent on said fluctuating values of said radius as a function of time during each heart cycle.

3. An analysis device as claimed in claim 2 wherein said evaluation means comprises comparator means for comparing said radius with a threshold value to identify said fluctuating values of said radius.

4. An analysis device as claimed in claim 3 wherein said evaluation means comprises means for determining a sequence of time intervals during which said radius is above or below said threshold, memory means for storing said sequence for each heart cycle, and means for identifying said abnormal conditions by comparing a most recently determined sequence with at least one sequence stored in said memory means.

5. An analysis device as claimed in claim 4 wherein said evaluation means comprises at one further comparator means for comparing said radius with at least one additional threshold value for identifying said fluctuating values of said radius.

6. An analysis device as claimed in claim 5 wherein said evaluation means comprises means for determining a further sequence in which said radius is above, below and between said threshold value and said at least one additional threshold value respectively, memory means for storing said further sequence for each heart cycle, and means for identifying abnormal conditions of said heart by comparing a most recently determined further sequence with at least one of said further sequences stored in said memory means.

7. An analysis device as claimed in claim 3 wherein said evaluation means comprises at one further comparator means for comparing said radius with at least one additional threshold value for identifying said fluctuating values of said radius.

8. An analysis device as claimed in claim 7 wherein said evaluation means comprises means for determining a sequence in which said radius is above, below and between said threshold value and said at least one additional threshold value respectively, memory means for storing said sequence for each heart cycle, and means for identifying abnormal conditions of said heart by comparing a most recently determined sequence with at least one of said sequences stored in said memory means.

9. An analysis device as claimed in claim 1 wherein said evaluation means comprises comparator means for comparing said radius with a threshold value to identify said fluctuating values of said radius.

10. An analysis device as claimed in claim 9 further comprising means for setting said threshold value to a value related to a maximum of said radius occurring during a current heart cycle of said heart.

11. An analysis device as claimed in claim 10 wherein said evaluation means comprises means for determining a sequence during which said radius is above or below said threshold, memory means for storing said sequence for each heart cycle, and means for identifying said abnormal conditions by comparing a most recently determined sequence with at least one sequence stored in said memory means.

12. An analysis device as claimed in claim 11 wherein said evaluation means comprises at one further comparator means for comparing said radius with at least one additional threshold value for identifying said fluctuating values of said radius.

13. An analysis device as claimed in claim 12 wherein said evaluation means comprises means for determining a further sequence in which said radius is above, below and between said threshold value and said at least one additional threshold value respectively, memory means for storing said further sequence for each heart cycle, and means for identifying abnormal conditions of said heart by comparing a most recently determined further sequence with at least one of said further sequences stored in said memory means.

14. A heart stimulator comprising:

pulse generator means for generation and emitting stimulation pulses;

electrode means, connected to said pulse generator means, for delivering said stimulation pulses to heart tissue of a heart;

measurement means for generating a measurement signal related to electrical activity of a heart;

differentiating means, connected to said measurement means and receiving said measurement signal therefrom, for forming a first derivative of said measurement signal;

evaluation means, connected to said measurement means and to said differentiating means and receiving said measurement signal and said first derivative of said measurement signal respectively therefrom, for plotting said measurement signal relative to said first derivative as coordinates in a coordinate system to obtain a resulting curve having a radius from said curve to an origin of said coordinate system, said radius exhibiting fluctuating values during each heart cycle of said heart, and for continuously monitoring said fluctuating values of said radius for identifying tachyarrhythmia of said heart dependent on said fluctuating values of said radius during each heart cycle; and means connected to said evaluation means and to said pulse generator means for controlling said pulse generator means to cause said pulse generator means to emit a pulse sequence designed to terminate said tachyarrhythmia when the presence of tachyarrhythmia is identified by said evaluation means.

15. A heart stimulator as claimed in claim 14 wherein said evaluation means comprises means for identifying tachyarrhythmia of said heart dependent on said fluctuating values of said radius as a function of time during each heart cycle.

16. A heart stimulator as claimed in claim 14 wherein said evaluation means comprises comparator means for comparing said radius with a threshold value to identify said fluctuating values of said radius.

17. A heart stimulator as claimed in claim 16 wherein said evaluation means comprises means for determining a sequence of time intervals during which said radius is above or below said threshold, memory means for storing said sequence for each heart cycle, and means for identifying said abnormal conditions by comparing a most recently determined sequence with at least one sequence stored in said memory means.

18. A heart stimulator as claimed in claim 17 wherein said evaluation means comprises at one further comparator means for comparing said radius with at least one additional threshold value for identifying said fluctuating values of said radius.

19. A heart stimulator as claimed in claim 18 wherein said evaluation means comprises means for determining a further sequence in which said radius is above, below and between said threshold value and said at least one additional threshold value respectively, memory means for storing said further sequence for each heart cycle, and means for identifying tachyarrhythmia of said heart by comparing a most recently determined further sequence with at least one of said further sequences stored in said memory means.

20. A heart stimulator as claimed in claim 19 wherein said evaluation means comprises means for determining a sequence during which said radius is above or below said threshold, memory means for storing said sequence for each heart cycle, and means for identifying said abnormal conditions by comparing a most recently determined sequence with at least one sequence stored in said memory means.

21. A heart stimulator as claimed in claim 20 wherein said evaluation means comprises at one further comparator means for comparing said radius with at least one additional threshold value for identifying said fluctuating values of said radius.

22. A heart stimulator as claimed in claim 21 wherein said evaluation means comprises means for determining a further sequence in which said radius is above, below and between said threshold value and said at least one additional threshold value respectively, memory means for storing said further sequence for each heart cycle, and means for identifying tachyarrhythmia of said heart by comparing a most recently determined further sequence with at least one of said further sequences stored in said memory means.

* * * * *